United States Patent
Cospito (10) Patent No.: US 11,278,371 B1
(45) Date of Patent: Mar. 22, 2022

(54) SURGICAL TABLE APPARATUS

(71) Applicant: Peter Cospito, Scotia, NY (US)

(72) Inventor: Peter Cospito, Scotia, NY (US)

(*) Notice: Subject to any disclaimer, the term of this patent is extended or adjusted under 35 U.S.C. 154(b) by 0 days.

(21) Appl. No.: 17/119,407

(22) Filed: Dec. 11, 2020

(51) Int. Cl.
*A61B 90/50* (2016.01)
*A61G 13/12* (2006.01)

(52) U.S. Cl.
CPC .......... *A61B 90/50* (2016.02); *A61G 13/126* (2013.01)

(58) Field of Classification Search
CPC .............................. A61B 90/50; A61G 13/126
See application file for complete search history.

(56) References Cited

U.S. PATENT DOCUMENTS 6,154,902 A * 12/2000 Russillio ................ A61G 7/065
5/623
8,214,952 B2 * 7/2012 Beasley ................ A61F 5/0193
5/648
8,955,179 B2    2/2015 Yu
9,211,099 B2   12/2015 Sampognaro
2016/0228317 A1 * 8/2016 Carn .................... A61G 13/128

FOREIGN PATENT DOCUMENTS

EP          1389958 B1     10/2008

* cited by examiner

*Primary Examiner* — Anita M King
(74) *Attorney, Agent, or Firm* — Hoffman Warnick LLC (57) ABSTRACT

A surgical table apparatus for a patient on a flat surface includes a platform including a main base. The main base includes a first end; a second end; a top surface; a bottom surface; two side surfaces extending from the first end to the second end, and extending from the top surface to the bottom surface; wherein a width of the main base at the first end is less than a width of the main base at the second end. The surgical table apparatus also includes at least two side surgical table wings, each side surgical table wing configured to be connected to respective ones of the two side surfaces of the main body. The first end is configured to be positioned at a groin area of the patient and the at least two side surgical table wings are configured extend over legs of a patient to define an extended surface.

20 Claims, 5 Drawing Sheets

SURGICAL TABLE APPARATUS

BACKGROUND

The disclosure relates generally to a surgical table apparatus. More particularly, this disclosure relates to a surgical table apparatus with a platform supported on an operating table or patient bed facilitating advancing medical devices in a body, including for advancing surgical tools in which installation and tools can be used smoothly manipulated.

BRIEF DESCRIPTION

A first aspect of the disclosure provides a surgical table apparatus for a patient. The surgical table apparatus includes a platform including a main base, the main base including a first end; a second end; a top surface; a bottom surface; two side surfaces extending from the first end to the second end and extending from the top surface to the bottom surface; wherein a width of the main base at the first end is less than a width of the main base at the second end. The surgical table apparatus also includes at least two side surgical table wings, each side surgical table wing configured to be connected to respective ones of the two side surfaces of the main body. The first end is configured to be positioned at a groin area of the patient and the at least two side surgical table wings are configured extend over legs of a patient to define an extended surface.

A second aspect of the disclosure provides surgical table apparatus for a patient on a flat surface. The surgical table apparatus includes a platform including a main base, the main base including a first end; a second end; a top surface; a bottom surface; two side surfaces extending from the first end to the second end, and extending from the top surface to the bottom surface; wherein a width of the main base at the first end is less than a width of the main base at the second end. The surgical table apparatus also includes at least two side surgical table wings, each side surgical table wing configured to be connected to respective ones of the two side surfaces of the main body; each side surface of the main body further includes elongated grooves and each of the at least two side surgical table wings further include a projection, wherein the projection of the wherein each of the at least two side surgical table wings are configured to be inserted in a frictional interference fit in a respective elongated groove of the main body. The surgical table further includes an extension table configured to be connected to the main body at the second end of the main body. The first end is configured to be positioned at a groin area of the patient and the at least two side surgical table wings are configured extend over legs of a patient to define an extended work surface.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION

As an initial matter, in order to clearly describe the current technology it will become necessary to select certain terminology when referring to and describing surgical procedures and apparatus. To the extent possible, common industry terminology will be used and employed in a manner consistent with its accepted meaning. Unless otherwise stated, such terminology should be given a broad interpretation consistent with the context of the present application and the scope of the appended claims. Those of ordinary skill in the art will appreciate that often a particular component may be referred to using several different or overlapping terms. What may be described herein as being a single part may include and be referenced in another context as consisting of multiple components. Alternatively, what may be described herein as including multiple components may be referred to elsewhere as a single part.

In addition, several descriptive terms may be used regularly herein, as described below. The terms "first", "second", and "third" may be used interchangeably to distinguish one component from another and are not intended to signify location or importance of the individual components.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Where an element or layer is referred to as being "on," "engaged to," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The present embodiments relate to a surgical table or surgical table apparatus (herein after "surgical table surgical table"). In particular, the present embodiments relate to a surgical table apparatus disposed at a position close to a patient during medical procedures. The medical procedures include, but are not limited to, procedures such as neurosurgical surgery, cardiovascular surgery, cerebral blood vessels and thoracic and abdominal blood vessels. These medical procedures often utilize surgical instruments and tools, many of which are specialized, elongated, for example scopes, catheters, optical fibers, or cutting devices.

In neurosurgical surgery or cardiovascular surgery, a catheter or the like may be inserted into a leg or a waist. In many cases, surgery is performed using a vein or an artery around the thigh where the catheter moves surgical devices, such as a scope or stent from the thigh area to an area of concern. The area of concern for surgery where the catheter moves surgical devices, includes but are not limited to the heart, lung, or other body regions.

The present surgical table apparatus may also be used in image guided diagnostic and therapeutic medical procedures. Image guided diagnostic and therapeutic medical procedures are often performed in a delicate manner with specialized instruments, such as but not limited to an elongate catheter and elongate guide wire(s). Examples of such procedures include, but are not limited to, vascular and interventional radiological procedures for endovascular treatment of cancers and cerebrovascular diseases, and angioplasty and stenting procedures for diseased vessels such as heart vessels. During such procedures, the operator, who may be a physician, surgeon, or other individual (hereinafter but in no manner limiting of the embodiments "physician"), inserts instruments, i.e., the catheter and guide wire into the patient's body to reach a target organ or area. The physician may remotely control the instruments outside the patient's body to operate on the target organ. The physician often monitors the operation through a monitor displaying the situation of the surgical area inside the patient's body.

Physicians often utilize a variety of techniques to control the elongate surgical tools, elongate instruments, and devices such as elongate catheters. As a catheter, endoscope, or other medical device (hereinafter but in no manner limiting of the embodiments "medical device") is advanced deeper into tortuous confines of a patient's vasculature, the medical device becomes correspondingly more difficult to control. Elongate lengths of wires, tubing, and the like are needed to guide the medical device into a patient. These elongate lengths of wires, tubing, and the like are generally laid across lower portions of the patient, surgical table, and/or patient and surgical table. However, a sterile surgical drape is typically strewn over the patient and/or surgical table to protect the sterility of the elongate lengths of wires, tubing, and the like, as well as the surgical tools, instruments and medical devices utilized therewith.

The performance of the operation often requires accurate tracking and precise positioning of the elongate catheter and guide wire at the target location. The accurate tracking and precise positioning of the elongate catheter and guide wire at the target location can be accomplished through line manipulation of the instruments and medical devices outside a patient's body. Such manipulation is currently performed by the physician with hands holding the instruments and resting on the patient's body.

A physician may hold the elongate catheter while resting their hand on the patient's body during fixation of the instruments. Simultaneously with resting their hand on the patient's body during fixation of the instruments, the physician can use their other hand to advance, withdraw, and/or rotate the elongate catheter, and/or guide wire, or other medical instruments. Such manipulation requires a learned degree of skill and dexterity to hold and control the elongate catheter and guide wire steadily at the same time.

In current practice the physician's hands tire quickly, which makes it more difficult for the operator to control the instruments precisely. Though the hands of the physician may rest on the patient's body or other relatively stable fixture, the body of a patient's surface is irregular and curved. Further, the patient's body may move from time to time due to pain suffered by the patient during the operation. Thus, the body of a patient's surface generally does not provide an adequate surface across which wires, tubing, and the like, as well as the surgical tools, instruments and medical devices utilized will readily pass. Snags, hold ups, impediments, or tangles can occur as the wires, tubing, and the like, as well as the surgical tools, instruments and medical devices utilized in the procedures, are moved across the body of a patient.

Additionally, as noted above, a sterile surgical drape may be strewn over the patient and/or surgical table. While the sterile surgical drape protects the sterility of the elongate lengths of wires, tubing, and the like, as well as the surgical tools, instruments and medical devices utilized therewith, it can also impair movement of the same. The sterile surgical drape generally does not present a smooth, flat surface either against the patient or against the table that the patient rests on for the procedure. Thus, as above with respect to the body of a patient's surface not providing an adequate surface across which wires, tubing, and the like, as well as the surgical tools, instruments and medical devices utilized will readily pass, the sterile surgical drape may present catches, snags, impediments, and obstacles. Therefore as the wires, tubing, and the like, as well as the surgical tools, instruments and medical devices utilized in the procedures are moved across the sterile surgical drape over a patient's body, the irregular and un-smooth sterile surgical drape may catch or impede movement of the wires, tubing, and the like, as well as the surgical tools, instruments and medical devices. As such, the catheters, guide wires, and other instruments cannot always be arranged in an orderly manner on the patient's body. Disorganization in medical procedures is not advantageous.

Accordingly, precise manipulation of elongated catheter and guide wires, as well as surgical tools, instruments and medical devices utilized in the procedures, is of high importance. The importance of precise manipulation of elongated catheter and guide wires, as well as surgical tools, instruments and medical devices utilized in the procedures is especially evident when the operation is conducted on blood vessels in the brain. In these operations, for example, physicians may require a stable working surface that can support their arms and hands.

Moreover, instruments with sharp points and edges which are placed on the patient's body may accidentally injure the patient. The patient's body may also be unintentionally exposed to fluids used for continuous irrigation of the instruments and medical devices during the operation.

Figure 1:
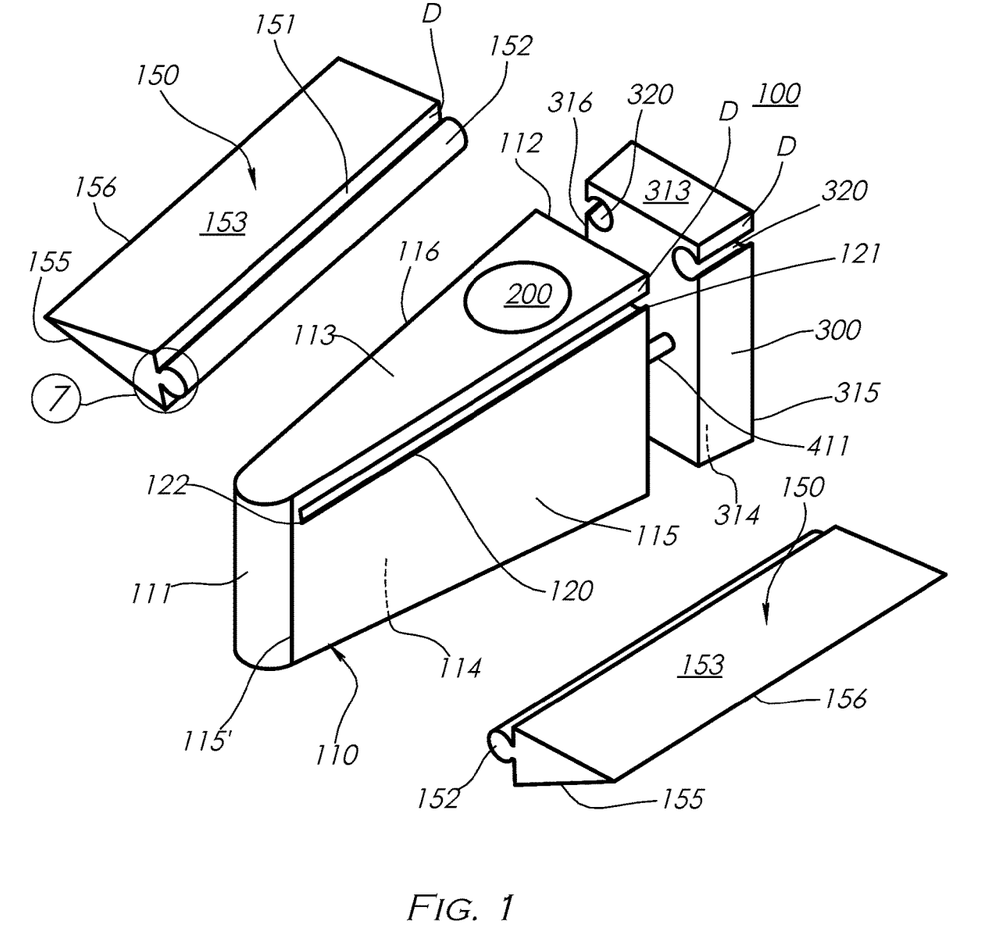
FIG. 1 illustrates an exploded perspective of a surgical table apparatus, in accordance with one aspect as embodied by the disclosure.
Figure 2:
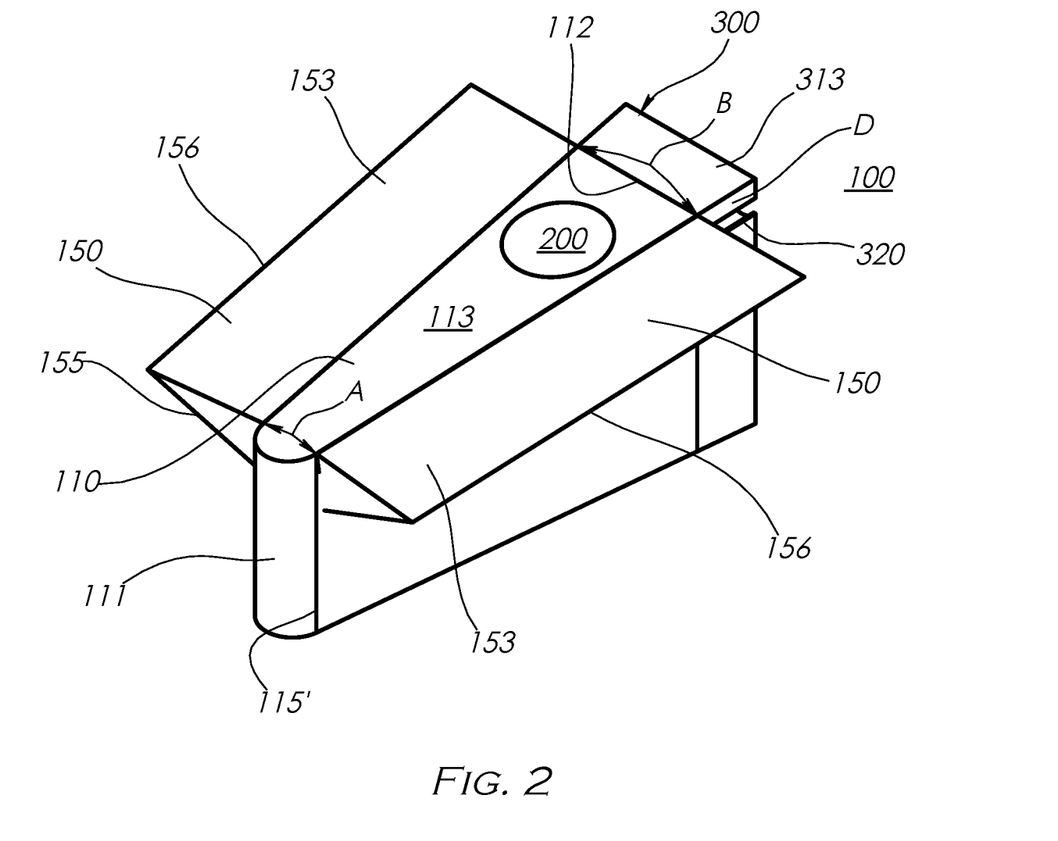
FIG. 2 illustrates an perspective of a surgical table apparatus with components connected, in accordance with one aspect as embodied by the disclosure.

As embodied by the disclosure, and with reference to the figures, in particular FIGS. 1 and 2, a surgical table apparatus 100 is configured to be placed on a flat surface, such as but not limited to an operating table or a patient bed. The operating or patient bed is not illustrated for facilitating description, and ease of illustration. Surgical table apparatus 100 as described herein can provide a large working surface for the physician to perform medical procedures. The medical procedures that the physician can perform include but are not limited to image guided diagnostic and therapeutic medical operative procedures. The surgical table apparatus 100, as embodied by the disclosure, can be easily disposed to the operating or patient bed. The surgical table apparatus 100 also can allow the physician convenient access to a patient's physiological features.

Accordingly, in certain aspects of present embodiments, the surgical table apparatus 100 includes a platform including a main base 110. Main base 110 is configured to be generally placed between legs of a patient. Main base 110 is supported on an upper side of a bed. Main base 110 includes a first end 111 that can be disposed closest to at groin area of a patient. First end 111 is curved at the end to enable the main base to fit closely as needed to a groin area of a patient. Main base 110 also includes a second end 112 disposed furthest from the groin area and proximate the feet and ankle region of a patient. Second end 112 is configured as a generally flat linear end for connection to other components of the embodiments of the surgical table apparatus 100, as described herein.

Figure 4:
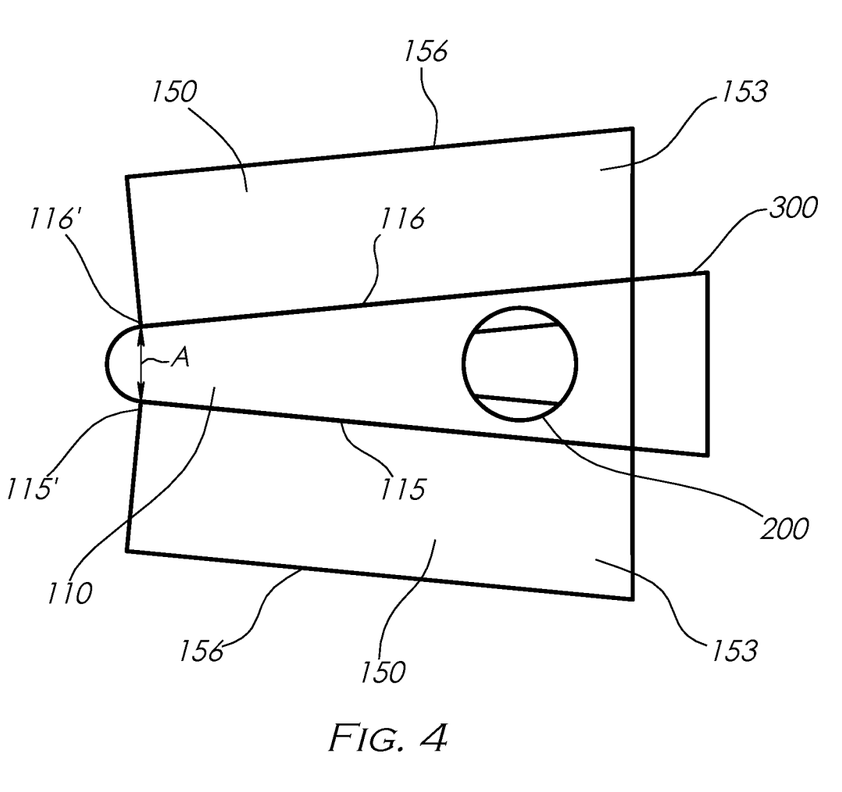
FIG. 4 illustrates a top view of a surgical table apparatus, in accordance with one aspect as embodied by the disclosure.

As illustrated in FIGS. 1, 2, and 4, first end 111 is curved. First end 111 curvature extends to and from sides 115, 116 of main base 110 of surgical table apparatus 100. First end 111 curvature presents a smooth transition from sides 115, 116 of main base 110 of surgical table apparatus 100 for comfort of the patient. Also, as first end 111 curvature presents a smooth transition from sides 115, 116, main base 110 of surgical table apparatus 100 is less likely to present structure to interfere with the physician handling and manipulation of medical devices and equipment, especially, but not limited to, elongated catheter and guide wires, as well as surgical tools, instruments and medical devices.

Figure 3:
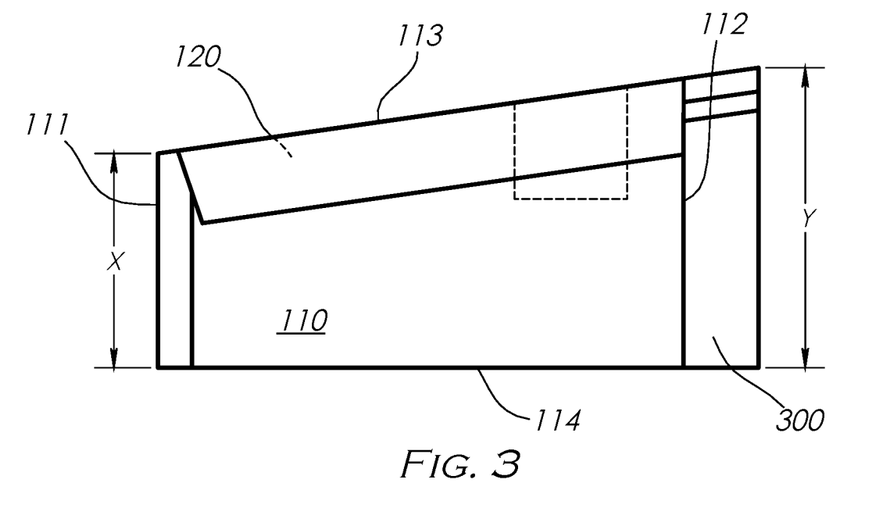
FIG. 3 illustrates a side view of a surgical table apparatus, in accordance with one aspect as embodied by the disclosure.

As illustrated in FIG. 3, first end 111 of main base 110 has a first end height X. First end height X is provided at a height X to be larger than most upper thigh and groin heights of a patient so a declining ramped upper surface 113 at its first end 111 extends over a prone patient's upward extent of the body at near the upper thigh and groin heights. Further, second end 112 of main base 110 is provided at a height Y selected to be larger than most feet, heel to toe. Thus, when a patient is prone on their back and feet are extended away from the operating table or patient bed, declining ramped upper surface 113 at its second end 112 extends over a prone patient's upward extent of the feet.

Thus, as illustrated, with first end height X is smaller than second end 112 height Y, main base 110 presents a declining ramped upper surface 113 with the ramp descending to the patient at a patient's groin area. Declining ramped upper surface 113 is free of any protrusions or impediments that would obstruct movement of equipment toward the patient. Accordingly, declining ramped upper surface 113 facilitates a physician extending and inserting medical devices toward the patient, as the declining ramped upper surface 113 does not require significant forces by a physician to move the medical devices up and into the patient.

As illustrated in FIGS. 1 and 2, main base 110 includes a first dimension A at first end 111. Main base 110 also includes a second dimension B at second end 112. First dimension A is smaller than second dimension B. First dimension A is determined where sides 115, 116 transition from a planar configuration at transition points 115', 116' as illustrated in FIG. 4.

Therefore, main base 110 presents an essentially triangular configuration (see top view in FIG. 4). The essentially triangular configuration extends from "apex" at first end 111 to a base at second end 112. Thus, main base 100 can be placed comfortably and conveniently between a patient's legs with first end 111 at the groin area and second end 112 at a remote patient position near feet where medical equipment and devices can be positioned in a ready state close but not interfering with the physician's access to the patient.

As also illustrated in FIG. 3, main base 110 includes a substantially flat, planar bottom surface 114. Substantially flat, planar bottom surface 114 will rest upon a bed or operating table. Accordingly, substantially flat, planar bottom surface 114 presents main base 110 with a stable and sturdy orientation between a patient's legs.

Main base 110 includes sides 115, 116 that extend from first end 111 to second end 112. Sides 115, 116 are substantially planar extending between first end 111 to second end 112 and also from declining ramped upper surface 113 to substantially flat, planar bottom surface 114. With the change of height from first height X to second height Y, sides 115, 116 have an essentially trapezoidal configuration.

Another aspect of the embodiments provides each of sides 115, 116 including a slot or groove 120. Slot or groove 120 (hereinafter "groove 120") includes an open end 121 at second end 112. Each groove 120 includes a closed end 122. Closed end 122 is positioned on the respective side and terminates just short of first end 111 and just before transition points 115' and 116'.

Grooves 120 are configured to be equally distant over their length from top surface 113 of main base 110 of surgical table apparatus 100. Grooves 120 are spaced a distance D from top surface 113 of main base 110 of surgical table apparatus 100 (FIG. 6).

Figure 5:
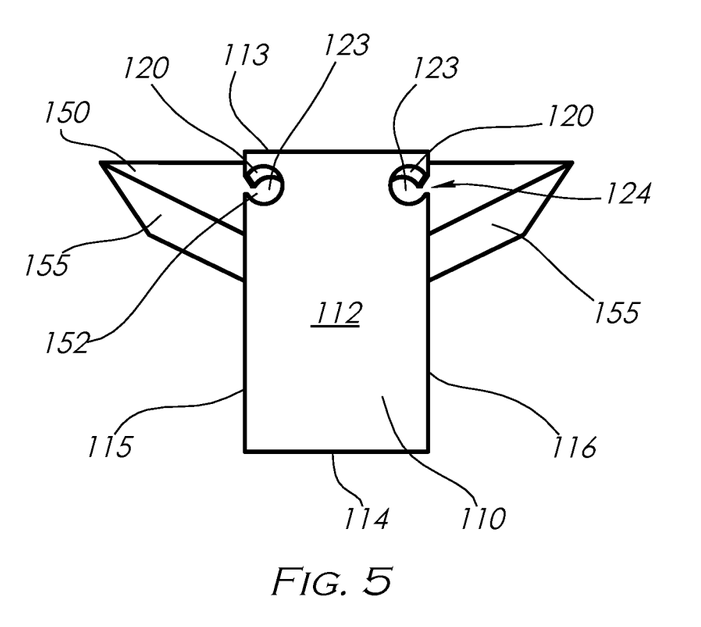
FIG. 5 illustrates a rear view of a surgical table apparatus main body second end, in accordance with one aspect as embodied by the disclosure.

Grooves 120 are configured and formed as a female connection 123 with a predetermined interior profile. As in the illustrated configurations, best visible in FIGS. 5 and 6, in one aspect of the embodiments, grooves 120 are formed with female connection 123 configured with a predetermined circular configuration that opens on side 115, 116 of main base 110. However, as embodied by the disclosure, female connection 123 can be formed with any convenient configuration to mate with retaining element 152 of side surgical table wing 150 (described hereinafter).

Figure 6:
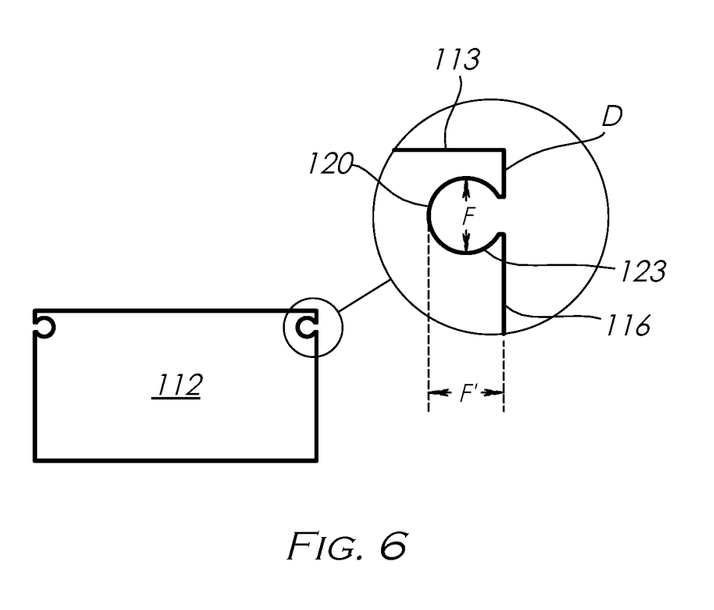
FIG. 6 illustrates a close up view of a groove formed in a rear end of the main body of the surgical table apparatus, in accordance with one aspect as embodied by the disclosure.
Figure 7:
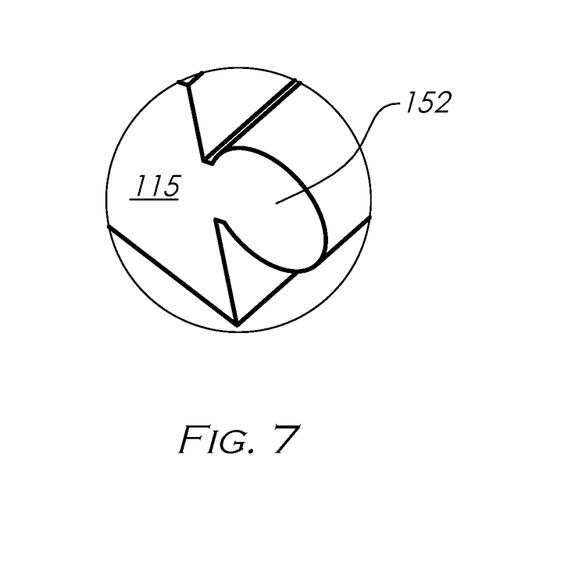
FIG. 7 illustrates a close up view of a projection formed on a side surgical table wing of the surgical table apparatus, in accordance with one aspect as embodied by the disclosure.

As illustrated, predetermined circular configuration has a diameter F extending between substantially flat, planar bottom surface 114 and declining ramped upper surface 113 (FIG. 6). However, where groove 120 opens to side 115, 116, the diameter F' of groove 120 is less than diameter F and presents groove access opening 124. As described herein, groove access opening 124 is sized to be just smaller than a neck of a male retaining element 152 of side surgical table wing 150. Accordingly, as a male retaining element 152 of side surgical table wing 150 enters groove 120, a frictional and interlocking fit can be achieved. Accordingly, this frictional and interlocking fit can secure male retaining element 152 of side surgical table wing 150.

As noted above, while the configuration of groove 120 is shown in a generally circular arrangement, the circular configuration is only on possible configuration within the scope of the embodiments. Interlocking male retaining element 152 and female connection 123 may be formed in any suitable interlocking and mating arrangement.

As embodied by the disclosure, surgical table apparatus 100 also includes two side surgical table wings 150. Each side surgical table wing 150 is configured to interlock with main base 110. To interlock with main base 110, each side surgical table wing 150 includes a male retaining element 152. Male retaining element 152 is formed in a complementary, interlocking, and frictional interconnection configuration with groove 120 of main base 110. Thus as noted above, as male retaining element 152 of side surgical table wing 150 enters groove 120, a complementary, interlocking, and frictional interconnection configuration is established. This complementary, interlocking, and frictional interconnection configuration secures male retaining element 152 of side surgical table wing 150 in groove 120 and extends main base 110 of surgical table apparatus 100 in a lateral orientation. Accordingly, when surgical table apparatus 100 is positioned in between legs of a patient and side surgical table wings 150 are fit into grooves 120, each side surgical table wing 150 of surgical table apparatus 100 are configured to extend over the legs of a patient.

Each side surgical table wing 150 includes a top surface 153. Top surface 153 of each side surgical table wing 150 is configured to be positioned coplanar with declining ramped upper surface 113. Each side surgical table wing 150 includes a wall 151. Wall 151 is positioned to abut a respective side 115, 116 of main base 110. Male retaining element 152 is formed on wall 151. As discussed above, grooves 120 are spaced a distance D from top surface 113 of main base 110 of surgical table apparatus 100.

In a similar spacing, male retaining element 152 is spaced a distance D from top surface 153 of side surgical table wing 150. Each male retaining element 152 can be slid into open end 121 of groove 120. Each male retaining element 152 can be slid in groove 120 until each male retaining element 152 abuts closed end 122 of groove 120. Thus, top surface 153 of side surgical table wing 150 and declining ramped upper surface 113 of main base 110 are then aligned, coplanar, and present an extended flat top surface for surgical table apparatus 100.

Each side surgical table wing 150 also includes a bottom surface 155 that extends at an angle from wall 151. Bottom surface 155 extends at an angle until it intersects and terminates at top surface 153. A side 156 of side surgical table wing 150 is configured to extend over the leg from approximately the patient's thigh and groin area to the patient's foot. The foot may be under the side surgical table wing 150 entirely, partially, or not at all. The side surgical table wing 150 provides an extended table for the physician to work on, manipulate tools and medical devices, and to facilitate the medical procedure or operation.

Figure 8:
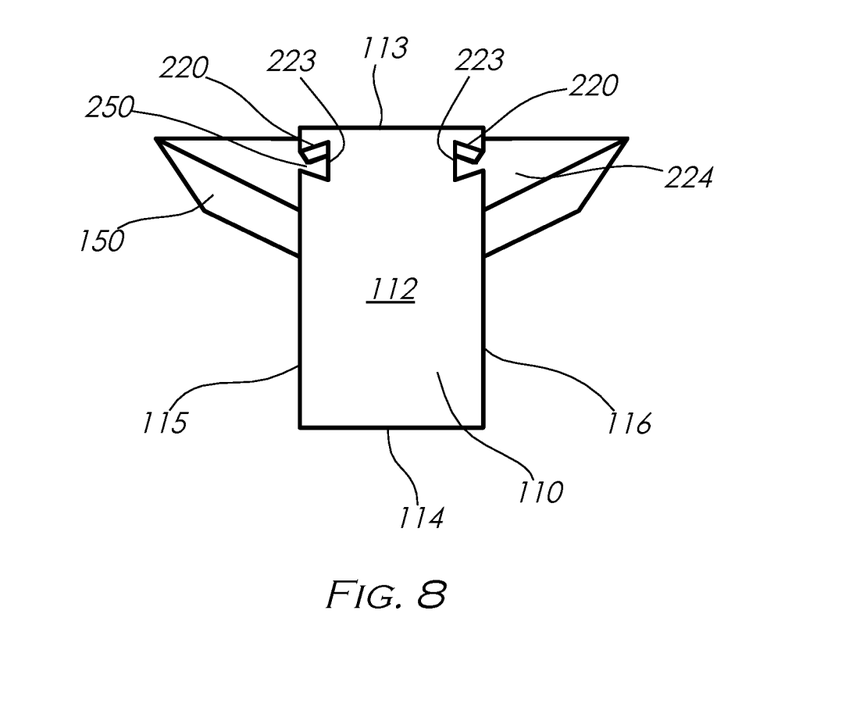
FIG. 8 illustrates a close up view of a further projection formed on a side surgical table wing of the surgical table apparatus, in accordance with one aspect as embodied by the disclosure.

FIG. 8 illustrates another configuration of the interlocking male and female connection. In FIG. 8, like reference characters represent like elements for ease of description and understanding. In FIG. 8, the interlocking male retaining element 250 can include a tenon or dovetail on side surgical table wing 150. Main base 110 of surgical table apparatus 100 includes a groove, which is formed as a truncated triangular groove 220. The base 223 of truncated triangular groove 220 is the wider part of truncated triangular groove 220. The truncated triangular groove 220 narrows to an apex at side 115, 116. Where truncated triangular groove 220 meets side 115, 116 a groove access opening 224 is formed. As with groove 120, groove access opening 224 is sized to be just smaller than a neck of a male retaining element 250 of side surgical table wing 150. Accordingly, as a male retaining element 250 of side surgical table wing 150 (described herein) enters groove 220, a frictional and interlocking fit is achieved to secure male retaining element 250 of side surgical table wing 150.

A further aspect of the embodiments can optionally provide a recess 200 in the surgical table apparatus 100. Recess 200 is provided to be a location for a physician to position medical devices, instruments, and the like. Also, recess 200 can be provided to accept a receptacle for solutions and other materials needed for the medical procedure or operation, such as but not limited to cardiovascular surgery.

As noted above, a surgical drape (not illustrated for facilitating understanding) may be provided over the patient. As surgical table apparatus 100 is employed in a medical procedure or operation, the surgical drape can be extended over the surgical table apparatus 100 and patient. If the surgical table apparatus 100 includes side surgical table wings 150, the surgical drape will extend over each of side surgical table wing 150. Surgical drape can extend over each of side surgical table wing 150 and can be spread evenly and tight on the surgical table apparatus 100. Thus, and instruments, elongated wires and scopes will avoid being caught or snagged on the drape and the drape can be smoothly and evenly disposed over the surgical table apparatus 100.

Further, if a surgical drape is provided and surgical table apparatus 100 includes recess 200, recess 200 can be used to further retain the surgical drape on the surgical table apparatus 100 and patient. For example and in no way limiting if the embodiments, a surgical drape can be spread over surgical table apparatus 100 and patient, and a portion of surgical drape can be tucked into recess 200. This tucking of the surgical drape into recess 200 may enhance retention of the surgical drape on the surgical table apparatus 100, including as medical instruments, elongated wires, and scopes and other devices are moved during the procedure.

Another aspect of the embodiments includes providing surgical table apparatus 100 with at least one extension table 300. Each extension table 300 can be positioned on main base 110 at the second end 112. Extension table 300 includes an extension top surface 313 that continues in a coplanar orientation from declining ramped upper surface 113. Extension table 300 can be continue the incline defined by main body 110 and thus be essentially an extension of main body 110. Alternately, extension table 300 can be essentially a cubic configuration with all equal dimensioned sides or rectangular cuboid with four equal and parallel sides and two sides that are parallel but not equal in dimension to the other four sides.

Extension table 300 may also include extension sides 315, 316 that continue sides 115, 116 of main base 110 in a coplanar configuration. Further, extension table 300 includes a bottom surface that extends bottom surface 114 of main base 110. For each surface or side of extension table 300, the surface or side is coplanar and coextensive with adjoining surface or side of main base 110. Accordingly, if surgical table apparatus 100 is provided with extension table 300, the overall combination of surgical table apparatus 100 and extension table 300 is essentially a longer version of main base 110.

Extension table 300 can also be provided with extension table grooves 320. Extension table grooves 320 are coextensive with grooves 120 of main base 110. Extension table grooves 320 are configured to have the same configuration of grooves 120, regardless if circular (FIG. 6) or interlocking male and female parts include a tenon or dovetail 250 (FIG. 8). Thus, each side surgical table wing 150 can slide into position in groove 120 abutting end 122 by aligning male retaining element 152 and groove 320. Next, each side surgical table wing 150 can be slid through groove 320 and then groove 3 until further sliding is prevented by the abutting of male retaining element 152 and end 122.

Main table 110 may include slots 410 that are aligned with extension rods 411 on extension table 300. Thus, in one aspect of the embodiments, extension rods 411 of extension table 300 are positioned in slots 410 of main base 110. Extension table 300 and main table 100 are then moved, at least one with respect to the other or both moved towards each other. Extension rods 411 will fit in slots 410 in an interference fit thus retaining extension rods 411 in slots 410, wherein main base 110 and extension table 300 are useable as a single entity.

As embodied by the disclosure, another aspect of surgical table apparatus 100 is that extension table 300 can be formed in any length to extend main base 110. Accordingly, surgical table apparatus 100 may be provided with multiple extension tables 300 of various lengths, although the Figures illustrate only one extension table for ease of understanding and facilitating understanding of the embodiments. The various lengths of extension table 300 will permit surgical table apparatus 100 to be used for varying procedures without concern for a size of a needed table length.

Further, as embodied by the disclosure, in the above embodiments, main base 110 and table portions 150 and 250 may be configured to be attachable by hook and loop fastener system (such as but not limited to Velcro) or a known coupling method, respectively, in addition to the other connection structures disclosed herein. Moreover, main base 110 and extension table 300 may also be configured to be detachable by a hook and loop fastener system (Velcro) or a known coupling method, respectively.

The surgical table apparatus 100 and its components, side surgical table wing 150 and extension table 300 may be formed from a lightweight material. The lightweight material will enable surgical table apparatus 100 and components, side surgical table wing 150 and extension table 300, to be easily maneuvered for positioning and use. One lightweight material for surgical table apparatus 100, side surgical table wing 150 and extension table 300, can include a synthetic foam, natural material, or combination of both. Illustrative, but not limiting, foams that can be employed to form for surgical table apparatus 100, side surgical table wing 150 and extension table 300, include polyurethane, expanded polystyrene (EPS), extruded polystyrene (XPS), polyisocyanurate, or any other foam now known or hereinafter developed.

Moreover, surgical table apparatus 100 and its components, side surgical table wing 150 and extension table 300, can be formed with an outer surface or outer surface coating that is impermeable to fluids. Further, surgical table apparatus 100 and its components, side surgical table wing 150 and extension table 300 can be formed with an outer surface or outer surface coating that also provides hardness, toughness, and rigidity. By an outer surface coating that is capable of providing hardness, toughness, and rigidity to surgical table apparatus 100 and its components, side surgical table wing 150 and extension table 300, multiple re-uses of one surgical table apparatus 100 and its components, side surgical table wing 150 and extension table 300 are possible.

In addition, with the impermeability and hardness, toughness, and rigidity of a surgical table apparatus 100 and its components, side surgical table wing 150 and extension table 300, the surgical table apparatus 100 as embodied by the disclosure may be easily cleaned, sanitized without worry of cross contamination. An outer surface or outer surface coating for surgical table apparatus 100 and its components, side surgical table wing 150 and extension table 300, can be any polymeric material, including material used to form the overall surgical table apparatus 100 and its components, side surgical table wing 150 and extension table 300.

In another aspect of the embodiments, surgical table apparatus 100 and its components, side surgical table wing 150 and extension table 300, can be any formed from, coated with, and/or impregnated with self-sterilizing or antimicrobial materials. As embodied by the disclosure, self-sterilizing or antimicrobial materials, such as but not limited to, elastomeric polymers with highly effective, broad-spectrum antimicrobial properties. These self-sterilizing or antimicrobial materials may enable surgical table apparatus 100 and its components, side surgical table wing 150 and extension table 300 to kill a range of viruses and drug-resistant bacteria.

Thus, as embodied by the disclosure, materials for surgical table apparatus 100 and its components, side surgical table wing 150 and extension table 300 enable ready cleaning, sterilization, and disinfecting, thus enabling rapid deployment in hospital situations, including in emergency rooms, triage centers, and operating rooms.

In use, the surgical table apparatus 100 is placed in between legs of a patient, when the patient is laying on an operating table, bed, or the like. Side surgical table wings 150 can be attached to the main base 110 extending over legs and feet of a patient providing an extended surface for the physician and equipment to be used in the procedure, and extension table 300, if an extension table is provided. It is often the preference of the physician to provide one or more extension tables 300 to extend the entire length of the operating table, so as described herein, instruments to be utilized by the physician during any procedure can have a straight and unencumbered path to move along. Thereafter, a sterile drape can be disposed over the surgical table apparatus 100 and its components, side surgical table wings 150 and extension table(s) 300 for insuring a sterile environment for the procedure. Accordingly, for the procedure, the patient is on an operating table. The surgical table apparatus 100 and its components, side surgical table wing 150 and extension table 300 are positioned between and against the inner legs of the patient, on and over the legs and feet (if desired) of a patient. Then a sterile drape can be placed on all of the operating table, patient, and surgical table apparatus 100 and its components, side surgical table wing 150 and extension table 300. This arrangement provides for an enhanced and large sized working surface with a straight and essentially tangle free path for the physician to work and guide instruments and equipment into operational positions. Accordingly, the entirely of the surgical table apparatus 100 and its components, side surgical table wing 150 and extension table 300 can be known as a "Guidepath PSC" (platform supporting catheterization).

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise. "Approximately" as applied to a particular value of a range applies to both end values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A surgical table apparatus for a patient, comprising:
   a platform including a main base, the main base including:
   a first end;
   a second end;
   a top surface;
   a bottom surface;
   two side surfaces extending from the first end to the second end and extending from the top surface to the bottom surface; wherein a width of the main base at the first end is less than a width of the main base at the second end;
   at least two side surgical table wings, each side surgical table wing configured to be connected to respective ones of the two side surfaces of the main base;
   wherein the first end is configured to be positioned at a groin area of the patient and the at least two side surgical table wings are configured to extend over legs of a patient to define an extended surface.

2. The surgical table apparatus according to claim 1, wherein each side surface of the main base further includes elongated grooves.

3. The surgical table apparatus according to claim 1, wherein each of the at least two side surgical table wings further include a projection.

4. The surgical table apparatus according to claim 1, each side surface of the main base further includes elongated grooves and each of the at least two side surgical table wings further include a projection, wherein the projection of the wherein each of the at least two side surgical table wings are configured to be inserted in a respective elongated groove of the main base.

5. The surgical table apparatus according to claim 4, wherein the elongated grooves and the projections have complementary configurations.

6. The surgical table apparatus according to claim 5, wherein the elongated grooves and the projections have a circular cross section.

7. The surgical table apparatus according to claim 5, wherein the elongated grooves and the projections have a trapezoidal cross section.

8. The surgical table apparatus according to claim 4, wherein the elongated grooves and the projections have a frictional interference fit.

9. The surgical table apparatus according to claim 2, wherein each elongated groove opens at the second end and extends along each respective side surface of the main base.

10. The surgical table apparatus according to claim 9, wherein each elongated groove extends along each respective side surface terminates before the first end of the main base.

11. The surgical table apparatus according to claim 1, wherein a height of the main base is greater at the second end than a height at the first end of the main base.

12. The surgical table apparatus according to claim 1, wherein a top surface of each of the at least two side surgical table wings are coplanar with the top surface of the main body when the at least two side surgical table wings are connected to the main base.

13. The surgical table apparatus according to claim 1, further including an extension table configured to be connected to the main body at the second end of the main base.

14. The surgical table apparatus according to claim 13, wherein each side of the main base further includes elongated grooves, and the extension table includes grooves configured to be aligned with the elongated grooves of the main base, whereby the at least two side surgical table wings can be connected through the grooves in the extension table through the elongated grooves to the main base.

15. The surgical table apparatus according to claim 13, wherein the main body further includes slots at the second end and the extension table includes extension rods configured to be inserted into the slots to retain the extension table with the main base.

16. The surgical table apparatus according to claim 13, wherein the extension table includes a top surface that is coplanar with the top surface of the main base.

17. The surgical table apparatus according to claim 1, where the main body and the at least two side surgical wings are formed from a lightweight foam material.

18. The surgical table apparatus according to claim 17, wherein the main body and the at least two side surgical wings are formed from a lightweight foam material and include a hardened outer surface impermeable to liquids.

19. The surgical table apparatus according to claim 17, wherein the main base and the at least two side surgical wings include an antimicrobial material.

20. A surgical table apparatus for a patient, comprising:
   a platform, the platform including main base, the main base including:
   a first end;
   a second end;
   a top surface;
   a bottom surface;
   two side surfaces extending from the first end to the second end and extending from the top surface to the bottom surface; wherein a width of the main base at the first end is less than a width of the main base at the second end;
   at least two side surgical table wings, each side surgical table wing configured to be connected to respective ones of the two side surfaces of the main base;
   each side surface of the main base further includes elongated grooves and each of the at least two side surgical table wings further include a projection, wherein the projection of the wherein each of the at least two side surgical table wings are configured to be inserted in a frictional interference fit in a respective elongated groove of the main base; and the surgical table further including an extension table configured to be connected to the main base at the second end of the main base;

wherein the first end is configured to be positioned at a groin area of the patient and the at least two side surgical table wings are configured extend over legs of a patient to define an extended surface.

\* \* \* \* \*